(12) United States Patent
Lu et al.

(10) Patent No.: US 11,419,627 B2
(45) Date of Patent: Aug. 23, 2022

(54) VASCULAR PUNCH

(71) Applicants: 3R LIFE SCIENCES CORPORATION, Campbell, CA (US); Hsiao-Chien Lin, Kaohsiung (TW)

(72) Inventors: Pong-Jeu Lu, Kaohsiung (TW); Hsiao-Chien Lin, Kaohsiung (TW)

(73) Assignee: 3R LIFE SCIENCES CORPORATION, Campbell, CA (US)

( * ) Notice: Subject to any disclaimer, the term of this patent is extended or adjusted under 35 U.S.C. 154(b) by 0 days.

(21) Appl. No.: 17/034,036

(22) Filed: Sep. 28, 2020

(65) Prior Publication Data

US 2021/0007768 A1   Jan. 14, 2021

Related U.S. Application Data

(63) Continuation of application No. PCT/US2018/057625, filed on Oct. 26, 2018.

(51) Int. Cl.
*A61B 17/3205* (2006.01)
*A61B 17/00* (2006.01)

(52) U.S. Cl.
CPC .......... *A61B 17/32053* (2013.01); *A61B 2017/00424* (2013.01)

(58) Field of Classification Search
CPC ....... A61B 10/06; A61B 17/29; A61B 17/295; A61B 17/28; A61B 17/2816; A61B 17/282; A61B 17/2833; A61B 17/2841; A61B 17/285; A61B 17/2909; A61B 17/2804; A61B 2017/2908; A61B 2017/2919; A61B 2017/2901; A61B 2017/2902; A61B 2017/2941; A61B 2017/2945; A61B 2017/2939
See application file for complete search history.

(56) References Cited

U.S. PATENT DOCUMENTS

| | | | | |
|---|---|---|---|---|
| 1,219,726 A | * | 3/1917 | Gray | A47J 43/283 294/3 |
| 3,391,690 A | * | 7/1968 | Armao | A61B 17/2812 83/171 |
| 4,785,809 A | * | 11/1988 | Weinrib | A61B 10/0266 606/174 |
| 4,872,455 A | * | 10/1989 | Pinchuk | A61B 17/3201 606/174 |
| 4,961,430 A | | 10/1990 | Sheahon | |

(Continued)

OTHER PUBLICATIONS

International Search Report for PCT/US2018/057625 (Parent Application) dated Jan. 4, 2019, 3 pages.

(Continued)

*Primary Examiner* — Sarah A Simpson

(57) ABSTRACT

The invention discloses a novel vascular punch employing compressive normal force for tissue separation from a targeted vessel. This invention is particularly designed for making a large round hole without massive bleeding in vascular surgery. A clean, non-frayed hole-making guided by the normal force cutting principle is realized using a site-biting punch mechanism. The side-biting vascular punch comprises a U-shaped razor blade cutter, a backstop for receiving the cutter, and a linkage mechanism, forming an aligned line of contact for normal compression force generation and thereby severing tissue out of the targeted vessel.

4 Claims, 9 Drawing Sheets

(56) References Cited

U.S. PATENT DOCUMENTS

| | | | |
|---|---|---|---|
| 5,569,299 | A | 10/1996 | Dill et al. |
| 5,570,700 | A | 11/1996 | Vogeler |
| 5,683,408 | A | 11/1997 | De Laage De Meux et al. |
| 5,707,392 | A | 1/1998 | Kortenbach |
| 8,317,726 | B2 | 11/2012 | Timberlake et al. |
| 8,740,811 | B2 | 6/2014 | Fortems et al. |
| 9,498,193 | B2 | 11/2016 | Smith et al. |
| 9,526,479 | B2 | 12/2016 | Hugle et al. |
| 9,974,524 | B2 | 5/2018 | Frushour et al. |
| 10,016,184 | B2 | 7/2018 | Kapushion |
| 2005/0267336 | A1 * | 12/2005 | Bertolero .......... A61M 25/1027 600/219 |
| 2007/0265546 | A1 | 11/2007 | Porat et al. |
| 2008/0039740 | A1 | 2/2008 | Chiu et al. |
| 2009/0105608 | A1 | 4/2009 | Chiu et al. |

OTHER PUBLICATIONS

Written Opinion for PCT/US2018/057625 (Parent Application) dated Jan. 4, 2019, 1 pages.
Published International Application WO 2020/086089 A1 for PCT/US2018/057625 (Parent Application) dated Apr. 30, 2019.
International Search Report and Written Opinion for PCT/US2018/057625 (Parent Application) dated Jan. 4, 2019, 9 pages.
Written Opinion for PCT/US2018/057625 (Parent Application) dated Jan. 4, 2019, 1 page.
Published International Application WO 2020/086089 A1 for PCT/US2018/057625 (Parent Application) Apr. 30, 2019.

\* cited by examiner

VASCULAR PUNCH

CROSS-REFERENCE TO RELATED APPLICATIONS

This application is a continuation application of a co-pending PCT international application PCT/US2018/057625 filed Oct. 26, 2018, the disclosure of which is hereby incorporated by reference in its entirety.

BACKGROUND OF THE INVENTION

1. Field of the Invention

The present invention generally relates to vascular hole-making associated with cardiovascular surgery, and more specifically aims at making a large round opening, typically a hole with diameter greater than 6 mm, that cannot be satisfactorily made using the market available vascular punches.

2. Description of the Prior Art

Ventricular assist device (VAD) is a mechanical circulatory support modality that has advanced to a matured stage to be considered as the standard-of-the-care for treating advanced heart failure. Circulatory support is accomplished by either pulsatile or continuous-flow blood pumps, in which blood is first drawn from the heart, then pressurized or energized by the VAD and finally returned back to the human circulation.

This mechanical blood flow energization process requires an artificial flow passage (graft) that connects its first (inflow) end adjacent to the assist device and its second (outflow) end anastomosed on the wall of an artery. The success of VAD implantation relies on many factors, among which graft anastomosis has been a critical element variably influenced by surgical skills and special tools that are provided to help achieve a qualified anastomosis.

The VAD graft conduit, typically made by Dacron, Polytetrafluoroethylene (PTFE) or silicone, etc., can be connected to artery in an end-to-side fashion at ascending or descending aorta. The diameter of the said graft is large, generally in the range of around 15-20 mm in diameter. In surgery, surgeon first uses a scalpel to cut a sizable incision comparable to the hole diameter to be made on the aortic wall, followed by trimming the incision edges using scissors, and finally suture the graft periphery stitch-by-stitch onto the incised and enlarged edges of the vascular opening. The quality of end-to-side anastomosis usually relies on the vascular tools provided, skill of the surgeon, and surgical approach field allowed. For a surgeon to accomplish such an anastomosis, the size and cleanliness of the incision and the trimmed edge of the opened vascular wall is important. A too large or too small incision or an irregularly enlarged hole periphery may cause mismatch of the connected graft-to-host edges during suturing, resulting in a distorted or wrinkled connection of the anastomosed tissue layer. Poor end-to-side anastomosis may lead to peri-operative bleeding or constitute a source of post-operative thrombus formation at the uneven, wrinkled graft-to-host connection site. It is a shame that presently there exists no large aortic punch that can help surgeons to make a big, non-frayed hole, safely and effectively, as a good foundation guaranteeing a graft connection of high quality.

To date, aortic punch for creating a small hole (less than 6 mm in diameter perse) in the aortic wall has been invented and used in clinical applications, in particular in the coronary bypass surgery. Typically, these small surgical punches include an anvil rod slidably engaged with a cutting tube as the separation means. Anvil is first inserted into the aorta through a small incision made in the wall. Shearing force is then created by pulling together the anvil relative to the cutting tube which houses the anvil and its supporting rod with a tight clearance. Substantial force has to be exerted by finger and palm in order to accomplish the given hole-making mission. It was found clinically that the adventitia of the vessel is most difficult to be separated cleanly. Methods were suggested to overcome those difficulties encountered in surgical hole-making including a razor-like tube or an anvil cutter to increase the shearing force during cutting; introduction of relative rotation motion onto the sliding cutting action contributed by anvil and cutting tube engagement; and amplification of the shearing force via a pistol-like handle and trigger mechanism, among others.

The above mechanical principle and methods proposed in the prior art associated with small vascular punch cannot be extended to punching a large hole in the artery. The reasons are mainly two-fold. First, hemostasis becomes a problem when a large, 10 to 20 mm, incision is made on the artery. Massive bleeding will be incurred due to high arterial blood pressure in the presence of a large opening, and this bleeding type is not generally allowed in a cardiovascular surgery. Even if temporary stoppage of bleeding can be achieved, the subsequent anvil insertion will inevitably wide open the incision and cause more serious uncontrollable bleeding. Second, the mechanism providing the shearing force for tissue separation will not be applicable for cutting a much larger hole, because the cutting area where shearing force is applied may increase substantially, requiring a much larger hand pressure to be exerted, which is often beyond the manual force a human hand can easily supply.

For the abovementioned reasons, there is a need to invent a large vascular punch that employs a different cutting mechanism and design principle. During the making of a large opening on the artery, not only a quick and clean tissue separation is desired, but also the hemostasis has to be absolutely assured to avoid massive, uncontrollable bleeding.

SUMMARY OF THE INVENTION

It is an object of the claimed invention to provide a surgical instrument for making a large hole in blood vessels, wherein the cutout is clean and properly configured without fraying.

Another object of the invention is that, regarding the instrument described above, the force required to facilitate the punch action is not excessive and can be easily provided by a hand.

Still another object of the above described instrument is that the tissue cutout can be retained in the instrument after punch.

Yet another object of the invention is that hemostasis (no bleeding) is assured as the claimed invention is operable when used together with a partial clamp (hemostatic forceps) without mutual interference.

In accordance with the above design requirements, the present invention envisions a vascular punch comprising a side-biting cutter set and a handler that amplifies the cutting force exerted manually by hand. The side-biting cutter set consists of a U-shaped razor blade and a backstop as depicted generically in FIG. 1a and FIG. 1b. Unlike the conventional vascular punch that employs shearing force for separating tissue, the present side-biting punch utilizes normal force to obtain a clean cut. The normal stress acting on the subject tissue to be severed is the applied force F divided by the foremost normal contact area A of the razor blade edge. This cutting contact force is extremely large in general because the blade edge is usually extremely thin. In the side-biting cutter design the contact pattern and characteristics of the cutting edge with respect to the supporting backstop hold the key of achieving a clean cut.

Illustrated in FIGS. 2a, 2b and 2c are three fundamental failure modes that adversely influence the side-biting cutting effectiveness. The Failure Mode A depicts a situation wherein the contact of the razor blade with the backstop is incomplete. It is assumed that the backstop surface is not completely rigid and the razor blade can cut into a shallow surface layer of the backstop, forming a zone rather than a point of contact. Within the contact zone a clean cut is obtained; however, this partial contact generates a reaction force that prevents the rest part of the cutting edge from engaging onto the backstop surf ace, thereby leading to a failed clean cut. Failure Mode A indicates the importance of the parallelism of the backstop surface to the razor cutting edge despite that the razor edge and the backstop surface are perfectly straight. Failure Mode A is practically attributed to the imprecision in fabrication and/or error committed in assembly of the handler.

On the other hand, Failure Mode B illustrates the incomplete contact caused by serration-like cutting edge of the razor. Similarly, Failure Mode C represents a backstop surface having an insufficient surface flatness when brought to contact with a perfectly aligned, straight razor edge.

In both Failure Modes B and C the cutting force only exerts on the contact zone, leaving the non-contact zone free of cutting force generated and hence leads to a failed clean cut. Failure Mode A is associated with the manufacturing imprecision and assembly misalignment of the handler while razor blade edge and backstop surface are assumed ideal in configuration. Failure Modes B and C are caused by the manufacturing inaccuracy of the cutter set, which in principle cannot be eliminated and is actually dependent on the manufacturing method in addition to the machinery precision. Notice that the gap of incomplete contact shown in the above Failure Modes is exaggerated for illustration purposes the actual gap size that leads to cutting failure is generally in the range less than a hundred microns.

In the real-life application of the side-biting punch, these three failure modes coexist in cutting. Root cause of failure comes collectively from the non-parallelism of the joined levers on which mounted respectively with razor cutter and backstop, together with the non-smoothness or wavy-shaped edge profiles associated with backstop and razor edge Certain tight tolerance has to be fulfilled in manufacturing the handler, the razor blade and the backstop. Nevertheless, it would be impractical to ask a super tight tolerance in the manufacturing and assembly process. To overcome this practical difficulty, an effective remedy that mitigates the aforementioned combined failure modes is envisioned, which, for example, comes from the installation of a semi-rigid pad mounted on the backstop. This pad has to possess an appropriate surface hardness. Too soft in pad hardness may result in a failed cutting caused by jamming the tissue into the crevice created, rather than dissecting the tissue along cutting line. Too rigid in pad hardness, however, will prevent a full contact zone to be formed upon cutting, because the hard pad resists the initial landing zone of contact to further expand to cover the entire contact engagement required for a clean cut.

A representative side-biting cutter and backstop design is depicted in FIGS. 3a, 3b and FIGS. 4a, 4b, respectively. The cutter comprises a U-shaped razor blade, a seat and a locking mechanism, as shown in exploded view in FIG. 3a and in integrated view in FIG. 3b. The U-shaped razor is preformed and has various sizes to suit the need of punching different hole sizes in a vessel wall. The backstop, depicted in FIG. 4a and FIG. 4b, comprises a solid base support mounted with a semi-rigid pad, and an adjustable base mechanism. This cutting module pair can be mounted onto a force generation and transmission linkage structure, termed handler hereafter, to constitute a side-biting vascular punch.

The handler that is used to accomplish a side-biting punch comprises, but not limited to, a four-bar linkage type and a single-pivot type mechanism, as illustrated in FIG. 5 and FIG. 6, respectively. For the four-bar linkage type, as depicted in FIG. 5, the two levers containing said razor blade and said backstop, respectively, are engaged in a parallel manner By rotating the two hinged bars connecting the two levers, the distance between the razor edge and the backstop surface will gradually be reduced to zero when contact engagement is established. The razor edge is of a semicircular or any curved shape, with its two tail arms open. During cutting, the cutter and the backstop will approach each other forming a line of contact literally. The resulting normal stress along this contact line is in general extremely large and is sufficient to sever the tissue compressed along the contact line.

Such line contact between razor cutter edge and backstop can also be achieved by a single-pivot mechanism via a particular scissors-like angular design of the two joined levers, as shown in FIG. 9 and FIG. 10. Upon cutting, a line contact of the razor edge and backstop surface is formed at the closed position of the pivoted levers. Tissue separation is then accomplished based on the same side-biting cutting principle elucidated in the four-bar linkage punch.

Desired force amplification can be generated in accordance with the linkage mechanism characteristic to each handler design. Both four-bar linkage and single-pivot mechanism depicted in FIG. 5, FIG. 6, FIG. 9 and FIG. 10 are assumed rigid ideally. In practice, the constituent beam-like levers are not perfectly rigid when subjected to applied force. Different degree of bending deformation will be incurred depending on what materials and lever configuration (solid rod, thin-walled I-beam, U-beam, etc) are adopted in parts design and manufacturing. Deformation of the levers due to material elasticity will cause contact force be absorbed into the structural deformation, resulting in a non-uniform, sometimes insufficient cutting force distributed along the contact line, or a misalignment of the contact line engagement that jeopardizes a clean cut of the targeted tissues.

A preferred embodiment of the present invention envisions a side-biting vascular punch comprising a cutter lever and a backstop lever and a handler that connects these two levers, as illustrated in FIG. 5. The backstop lever is joined rigidly to a pistol-like base frame that is to be held in a palm of the user. There are two short hinge bars communicate with the cutter lever and the backstop lever, forming a four-bar linkage of parallelogram to facilitate the cutting action. A trigger lever that slidably engaged with the cutter lever by a pivot-in-a-slot mechanism will impart force for rotating the two hinge bars to result in a translational movement of the cutter lever relative to the backstop lever, as shown in FIG. 7 and FIG. 8. The cutter lever's forward translation motion will end with a contact line formed between the razor edge and the backstop surf ace upon encounter.

As contact line forms, the rotation of the hinge bars stops with the cutting force generated via the transmission of the hand gripping force through the four-bar-linkage mechanism. Tissue cutting is hence achieved followed by contact line formation and cutting force generation. The semi-rigid pad on the backstop will receive the razor blade in full and mitigate imperfection committed in manufacturing and assembly. Generally speaking, with appropriate hardness of pad provided, the razor blade will cut through the compressed tissue and further into some depth of the semi-rigid pad. The tissue severed from the vessel, hence, will remain captured in the space surrounded by the razor blade and the backstop when user finishes cutting and holds the trigger lever in the closed position. A clean cut of a hole on the vessel is thus accomplished and the tissue cutout can be safely transported outside of the human body along with the retrieval of the present invention.

Referring to FIG. 9 and FIG. 10 for an alternative embodiment of the present invention that envisions a side-biting vascular punch comprising a cutter lever and a backstop lever hinged together by a pivot, similar to that of a pair of scissors. These two levers are arranged in such a way that a line contact of the razor blade and the backstop surface will be formed when gripping force is applied to bring these two levers into the closed position for cutting. The single-pivot type punch design is more susceptible to errors committed in manufacturing and assembly than the four-bar linkage type. Error tends to be amplified at places situated distal to the pivot. When such a scissors-like punch is applied for tissue separation, the initial contact point or segment formed often lands over the proximal region to the pivot, namely, over the two arm ends of the U-shaped razor blade.

The gap between the razor edge and the backstop surface will enlarge, the larger the farther from the pivot, for the rest blade portion distal to the pivot, specifically those over the semi-circular part of the razor. As a result, the cutting becomes incomplete which frequently fails at the semi-circular portion of the razor blade distal to the pivot. A clean cut of tissue calls for a very accurate manufacturing of the parts and the assembly scheme as well. To mitigate this intrinsic failure in contact line formation, the backstop should be designed to be adjustable. Specifically, there is surface orientation mechanism that has to be provided During punch assembly, the cutter and backstop levers are first integrated around the pivot, and then the two levers are brought to their closed position with initial contact point or segment established. By adjusting the backstop surface orientation, a desired full contact line formation can be approximated with the cutting engagement attained maximally over the entire razor edge. Further with the aid of the semi-rigid pad for error mitigation, a clean cut can generally be accomplished as expected.

Different radius of curvature can be assigned for constructing the U-shaped razor blade for different size of hole to be punched on the vessel. Oval-shaped blade can also be custom made to meet specific requirement of graft connection. In clinical application of end-to-side anastomosis, the connected vessels or grafts assume different cross-sectional shapes depending on how the angle of graft-to-host connection is preferred. The present invention can serve this anastomotic purpose by providing a set of preformed razor blades conformal to the projected shape and size of the connected periphery to be sutured.

Maintaining hemostasis during hole-making is of paramount importance in surgery. The present side-biting punch works ideally with the existing partial occlusion tools In FIG. 11 and FIG. 12 show the integral use of the present side-biting punch with the hemostatic partial clamp. Prior to vascular hole-making, the targeted vessel is first partial clamped to create an isolated area ready for punch. In this isolated area the vessel wall is flattened and arterial blood flow blocked from entering this isolated area. Site-biting punch can be applied therein with the razor edge landed with a finite distance to the boundary of the clamped area (dotted line, FIG. 12). Such joint use arrangement is able to provide highly reliable hemostasis during and after the presently designed hole-making procedure.

BRIEF DESCRIPTION OF THE DRAWINGS

The cutting effectiveness and mechanical principle involved in the present invention, and other objects, features and advantages thereof, may be understood by reference to the following description taken in connection to accompanying drawings in which.

DETAILED DESCRIPTION OF THE PREFERRED EMBODIMENTS

Figure 5:
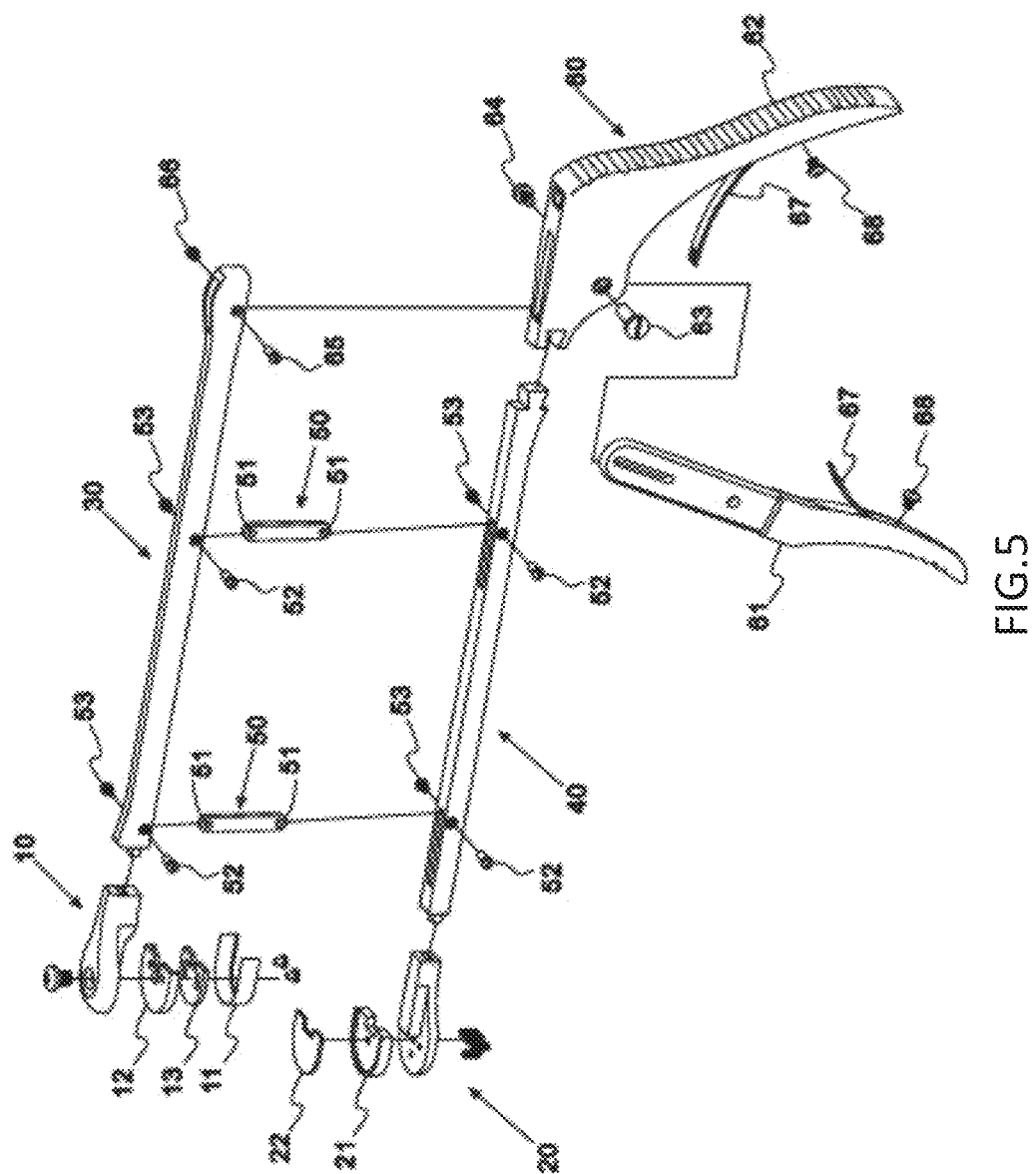
FIG. 5 is a blow-out view of a preferred embodiment of a four-bar linkage type side-biting punch design.
Figure 6:
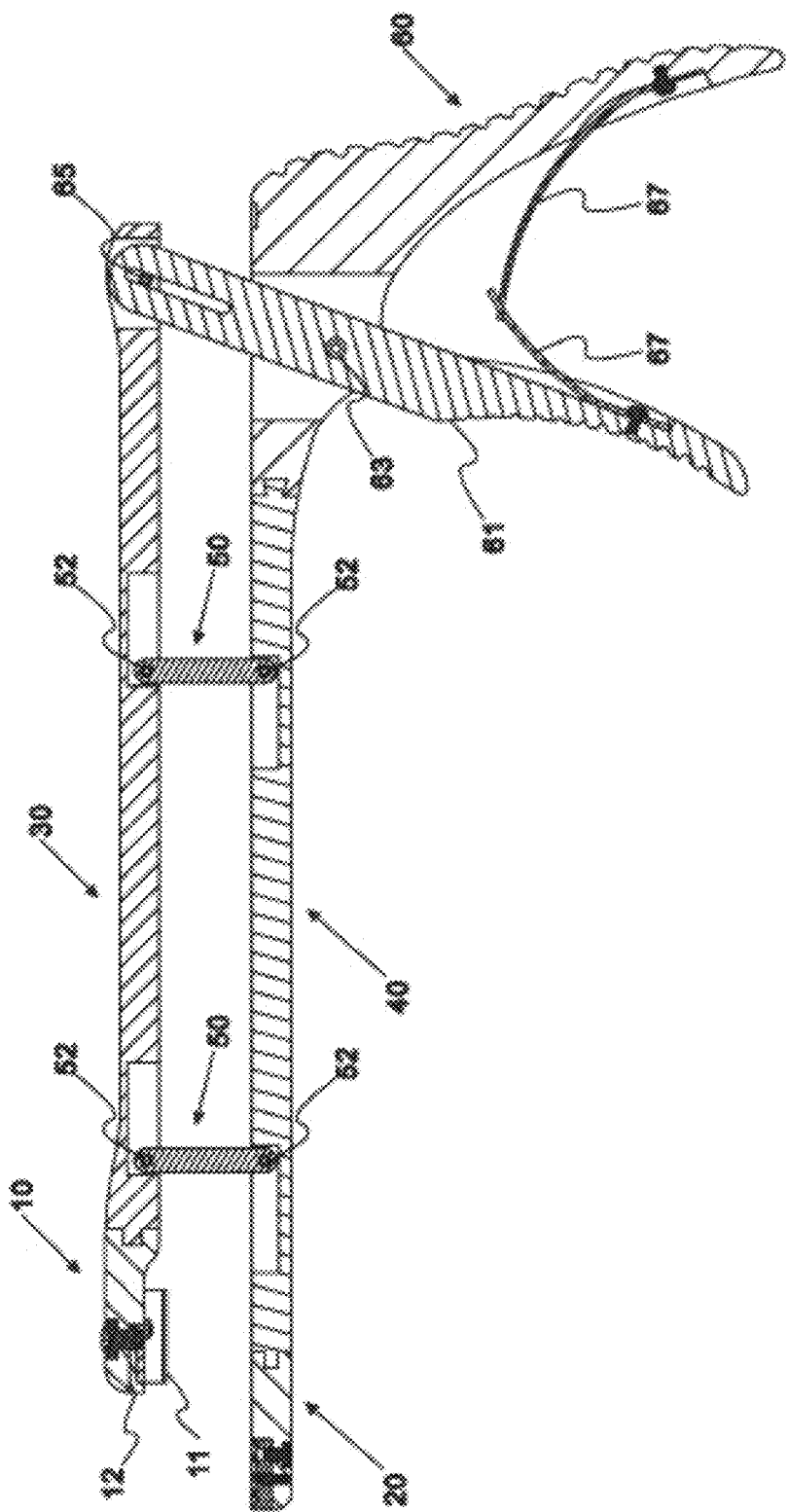
FIG. 6 is a sectional view of a preferred embodiment of a four-bar linkage type side-biting punch design.

Referring to FIG. 5 and FIG. 6 the four-bar linkage type side-biting vascular punch comprises a razor-blade cutter 10, a backstop 20, a cutter lever 30, a backstop lever 40, a pair of hinge bars 50, and a handler 60. The razor-blade cutter further comprises a U-shaped razor-blade 11, a seat 12 and a locking mechanism 13. As detailed in FIG. 3a, and FIG. 3b, the seat 12 is screwed fixed with cutter 10 by a screw 14, and the razor blade 11 is squeezed against the side flange of said seat 12 using a lock plate 13. In the installation of the razor blade 11, the dull edge of the blade is first placed in contact with the corner of the side flange of seat 12, and then the blade side wall is squeezed and retained in position by the lock plate 13, followed by fixing the lock plate 13 using two lock screws 15. The cutter 10 and backstop 20 are blood-contacting, hence preferred to be made single-use to eliminate the possibility of infection. When integrated, the cutter 10 becomes an integral extension of the cutter lever 30, requiring a tight assembly tolerance to assure the parallelism of the razor blade edge 11 to the cutter lever 30.

Figure 1A:
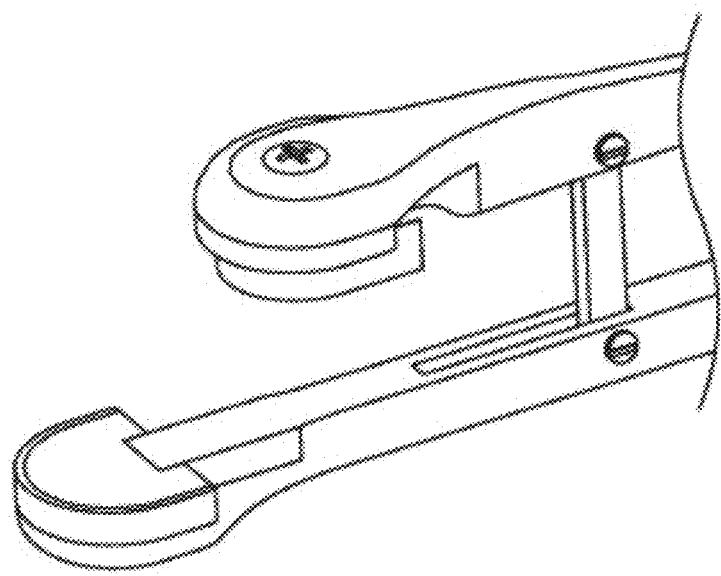
FIG. 1a is a schematic illustration of a side-biting punch mechanism involving a U-shaped razor cutter and a backstop supporting base for normal force generation upon cutting.
Figure 1B:
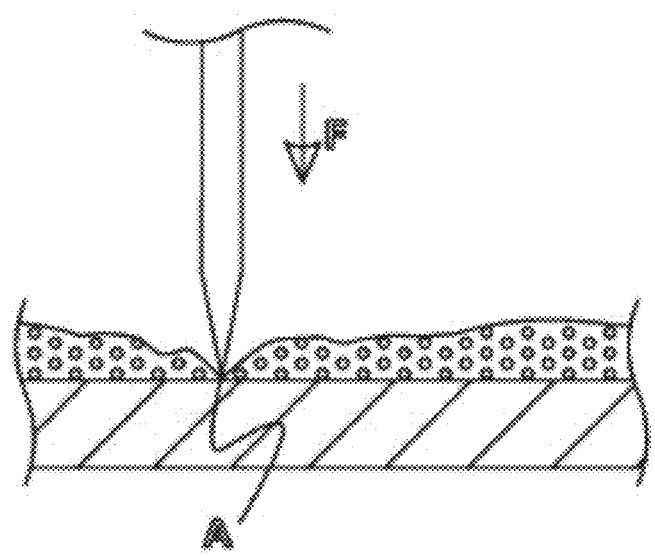
FIG. 1b is a sectional view of a razor blade engaged in tissue separation wherein normal cutting stress is generated by the applied force F divided by the edge area A.
Figure 2A:
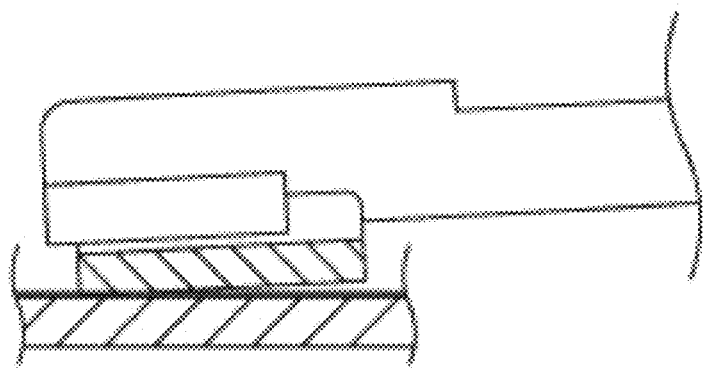
FIG. 2a shows Failure Mode A of side-biting punch, wherein the razor edge and backstop surface are misaligned, attributable to the error committed in the manufacturing or installation of the components of the handler, leading to an incomplete cutting line contact and tissue separation.
Figure 2B:
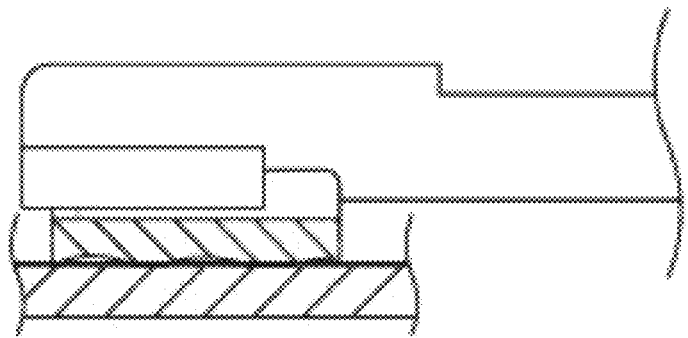
FIG. 2b shows Failure Mode B of side-biting punch, wherein the razor edge is wavy due to manufacturing error, leading to an incomplete cutting line contact and tissue separation.
Figure 2C:
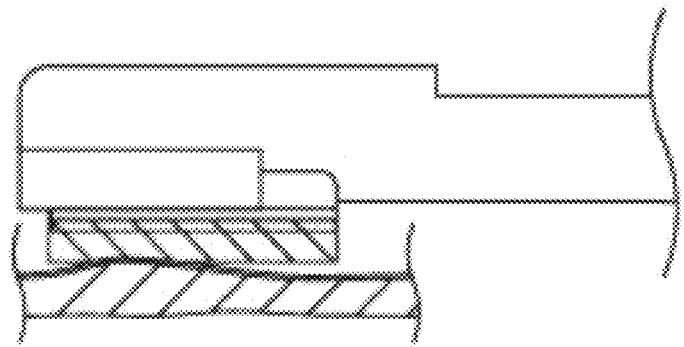
FIG. 2c shows Failure Mode C of side-biting punch, wherein the backstop surface is not uniformly flat due to manufacturing error, leading to an incomplete cutting line contact and tissue separation.
Figures 3A, 4A:
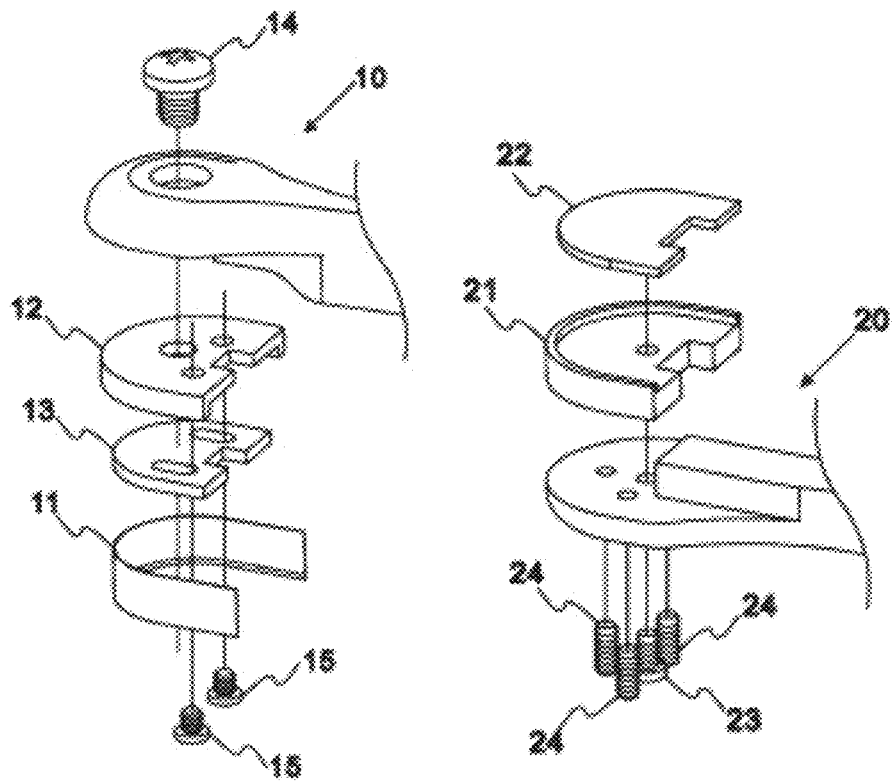
FIG. 3a is a representative side-biting cutter design comprising a U-shaped razor blade, a seat and a locking mechanism, shown in a blow-out view.
FIG. 4a is a representative backstop design comprising a solid base, a semi-rigid pad and an adjustable pad platform, shown in a blow-out view.
Figures 3B, 4B:
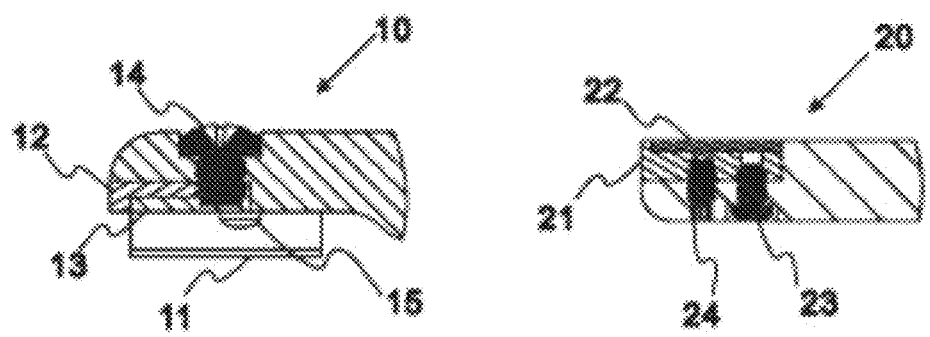
FIG. 3b is a representative side-biting cutter design comprising a U-shaped razor blade, a seat and a locking mechanism, shown in a sectional view.
FIG. 4b is a representative backstop design comprising a solid base, a semi-rigid pad and an adjustable pad platform, shown in a sectional view.

The backstop 20, however, includes a supporting base 21 glue attached with a semi-rigid pad 22. In FIG. 4a and FIG. 4b illustrated the construction of said backstop 20 Supporting base 21 is connected with the backstop 20 by using a lock screw 23, further augmented by three set screws 24 for surface orientation adjustment so as to attain the optimized line of contact during cutting. Analogous to the integration of cutter 10 to cutter lever 12, the alignment in assembly of backstop 20 and backstop lever 40 is required to be within certain tight tolerance also.

The backstop lever 40 is rigidly connected to the handler 60 and the cutter lever 30 is slidably coupled with the handler 60 in a pivot-in-a-slot manner. A pair of hinge bars 50, each comprising a short pin with two through holes 51 bored at its two ends, are rotatably joined with the cutter lever 30 and backstop lever 40, forming a four-bar-linkage mechanism. The rotational motion of the hinge bar is provided through the use of two pairs of pivot 52 and its lock screw 53, connecting together cutter lever 30 and backstop lever 40 via a rotational constraint.

Figure 7:
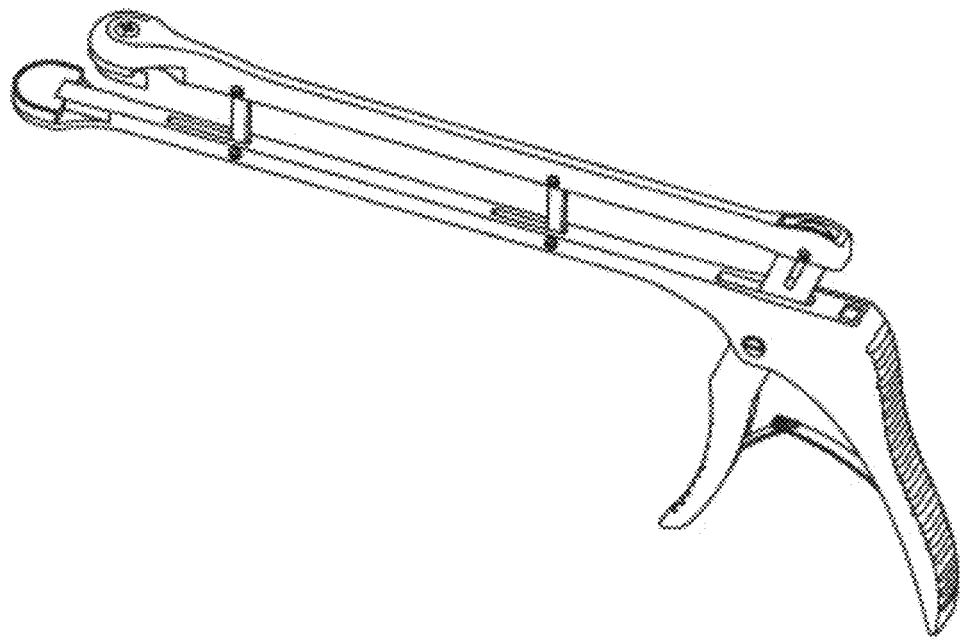
FIG. 7 is a perspective view showing the four-bar-linkage type vascular punch in an open position ready for use.
Figure 8:
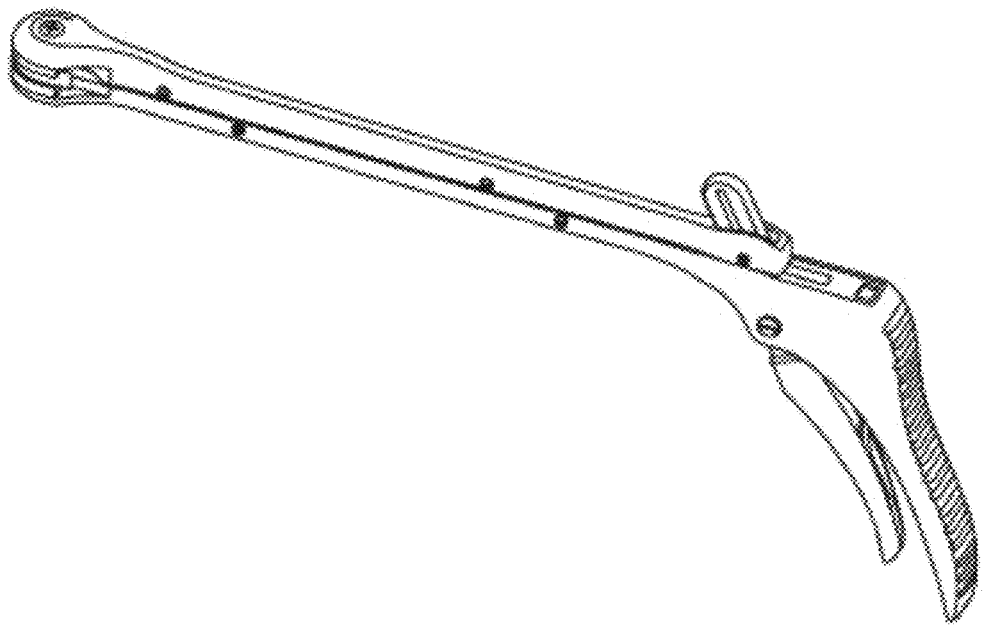
FIG. 8 is a perspective view showing the four-bar-linkage type vascular punch in a closed position with side-biting punch action completed.

The four-bar-linkage in cocked, ready-to-use open position and retracted, cutting completion closed position are illustrated in FIG. 7 and FIG. 8, respectively. This four-bar-linkage mechanism gives rise to a translational motion of cutter lever 30 parallel to backstop lever 40, by way of a simultaneous rotation of the two hinge bars 50. Parallelism between the joined levers 30 and 40 holds the key of an effective side-biting punch intended to remove vascular tissue in surgery. Parameters influencing the parallelism include the pivot hole positions drilled on hinge bars 50, cutter 30 and backstop levers 40; the fitting tolerance of hinges 50 assembled with the rotationally engaged parts 30, 40; and the rigidity of the connected levers 30, 40, when subject to cutting force generated from manually gripping the trigger 61 toward handset 62 of handler 60.

U-beam structure is preferred for constructing cutter lever 30 and backstop lever 40, because these thin-walled structures may optimize the weight penalty against maximal bending stiffness attained for the lever rigidity. Tigger 61, rotationally mounted on the handler 60 by a pivot 63 and its pivot screw 64, constitutes a mechanism for imparting cutting force onto and translational motion associated with the cutter lever 30 of the said side-biting punch. The cutter lever 30 is joined with the slot in trigger 61 by a pivot 65 fixed on the cutter lever 30 by a screw 66, forming a pivot-in-a-slot relationship with the distal portion of the trigger 61, wherein a slot is provided for accommodating the pivot 65.

The cutter lever 30, hence, can be pushed forward from the cocked position to the closed position, and vice versa from the closed position back to the cocked position. Force required for forward motion is provided by hand gripping whereas backward motion by the recoil force generated by a leaf spring 67 pair whose legs are fixed by screw 68 on the handset 62 and the trigger 61, respectively. As trigger 61 is actuated with circular motion induced, centered around pivot 63, the distal slot of the trigger 61 guides the cutter lever 30 moving forward or backward and drives the actuated pivot 64 sliding in the slot, consequently results in the rotation of the hinge bars 50 and brings the cutter lever downward or upward correspondingly. Hand gripping trigger 61 toward handset 62 initiates the cutting action and brings cutter lever 30 downward, until razor blade edge 11 lands on the backstop surf ace for cutting the compressed tissue underneath the contact line. Upon completion of cutting, the user holds the present invention in the closed position, hence securing the removed vascular tissue and letting it well captured in the space defined by the inner side of the razor blade 11 and the backstop 20. Consequently, tissue can be safely retrieved after pulling the present invention outside of the patient's body.

Figure 9:
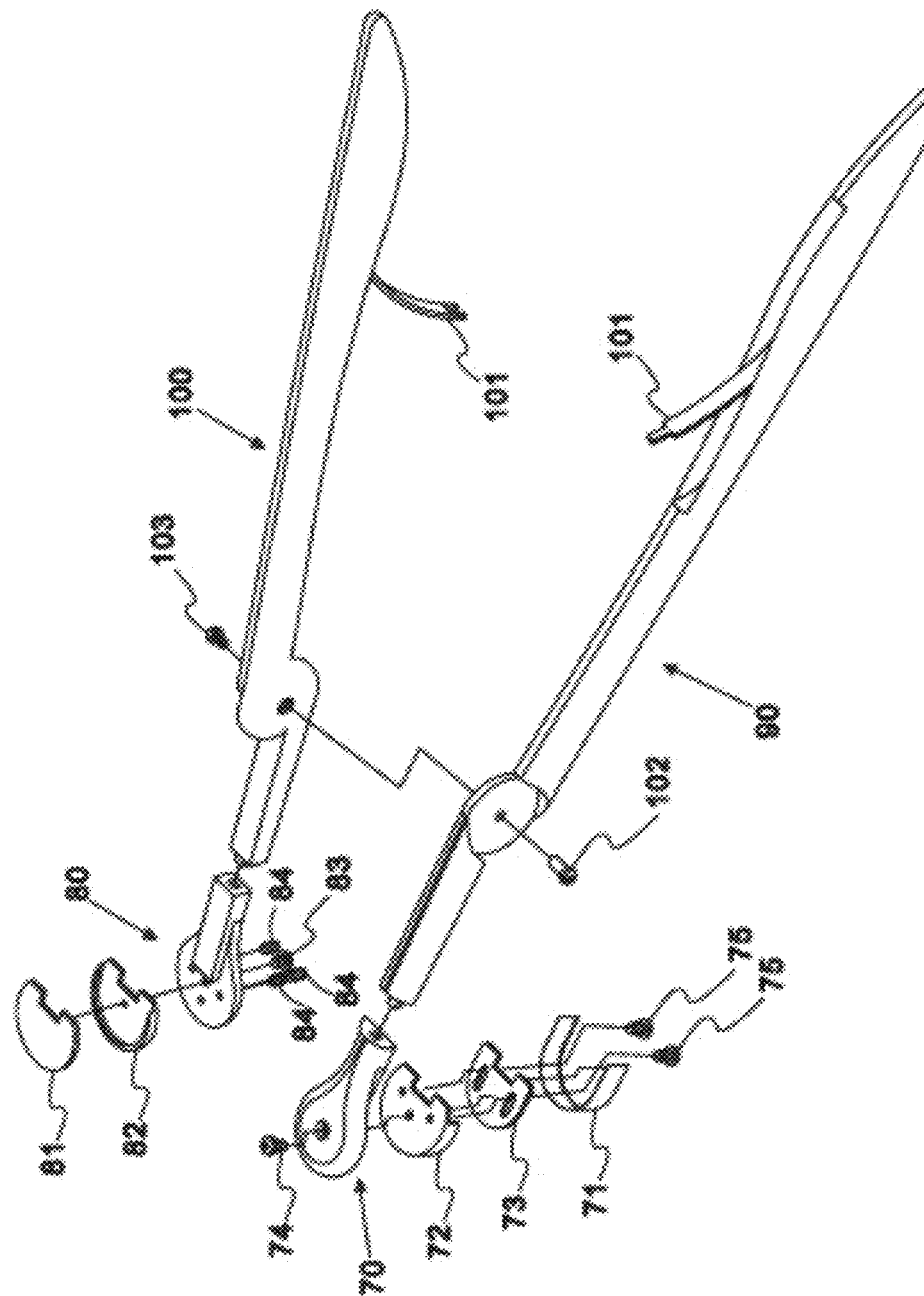
FIG. 9 is a blow-out view of another embodiment of a single-pivot type side-biting punch design.
Figure 10:
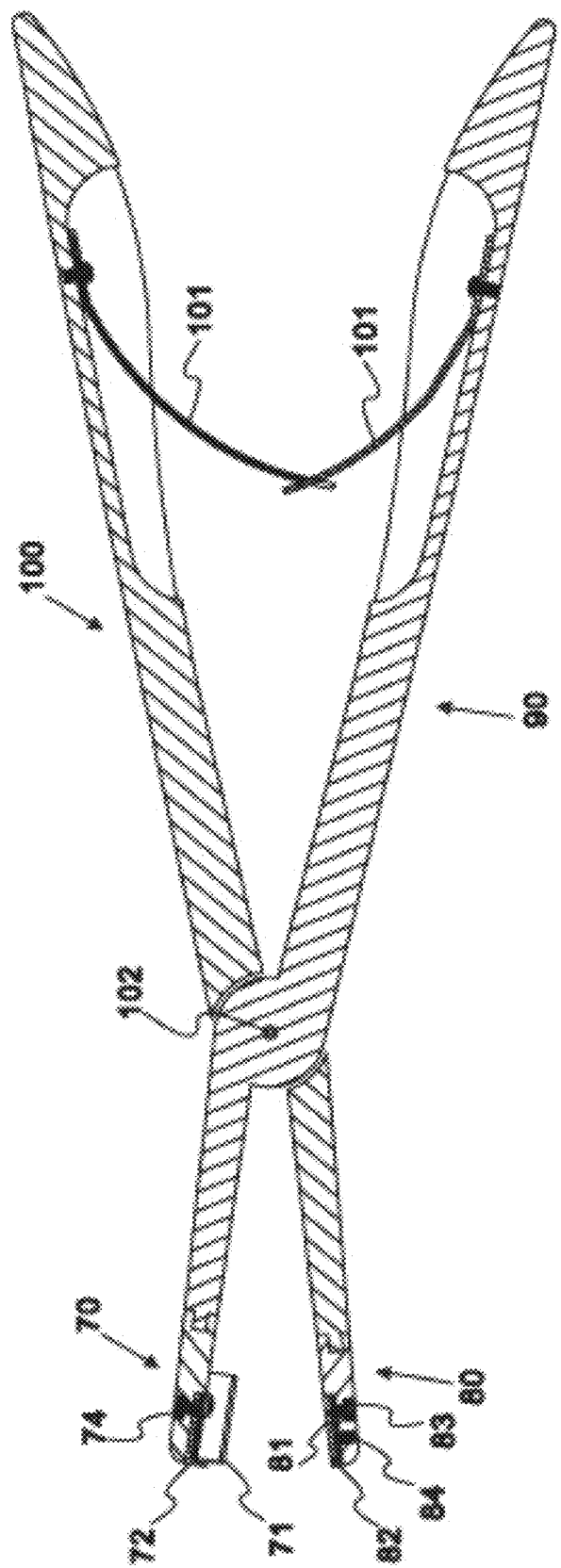
FIG. 10 is a sectional view of another embodiment of a single-pivot type side-biting punch design.

Another embodiment of the present invention is via a single-pivot type mechanism, as illustrated in FIG. 9 and FIG. 10. This said single-pivot type side-biting punch comprises a razor blade cutter 70, a backstop 80 preferred to be adjustable, a cutter lever 90, a backstop lever 100, a leaf spring pair 101, and a pivot 102 and its lock screw 103. The razor blade cutter 70 comprising a razor blade 71, a seat 72, a lock plate 73, a lock screw 74, and two set screws 75, is of the same design as previously described in the four-bar-linkage side-biting punch. This razor blade cutter 70 is rigidly integrated with the distal end of the cutter lever 90, and so is the backstop 80 to the backstop lever 100. Cutter lever 90 and backstop lever 100 are joined together by a pivot 102 and a pivot screw 103, into a scissors-like structure that allows gripping force to be amplified and transmitted to the razor cutting edge. Such single-pivot type side-biting punch aligns the contact line of the razor edge with the backstop surface when the said punch is brought into the closed position for cutting.

The adjustable backstop 80 is of the same design as the backstop 20 described previously in the four-bar-linkage realization. For this adjustable backstop 80, pad orientation adjustment can be attained by, but not limited to, a pad platform 82 glue attached with the semi-rigid pad 81, the pad platform 82 being initially loosely joined with the supporting base of backstop 80 using a lock screw 83 threaded in from the exterior side of the pad platform 82 There are three additional set screws 84, each occupying a vertex of a triangle, that are threaded in the supporting base of backstop 80 for surface orientation adjustment. By independently adjusting the depth of the threaded set screws 84 together with the lock screw 83, the contact line of cutting can be re-oriented to result in a full contact of the razor edge with the semi-rigid pad 81, hence enhancing the cutting effectiveness.

Assurance of hemostasis during large vascular hole-making is of paramount importance to a surgical operation.

Figure 11:
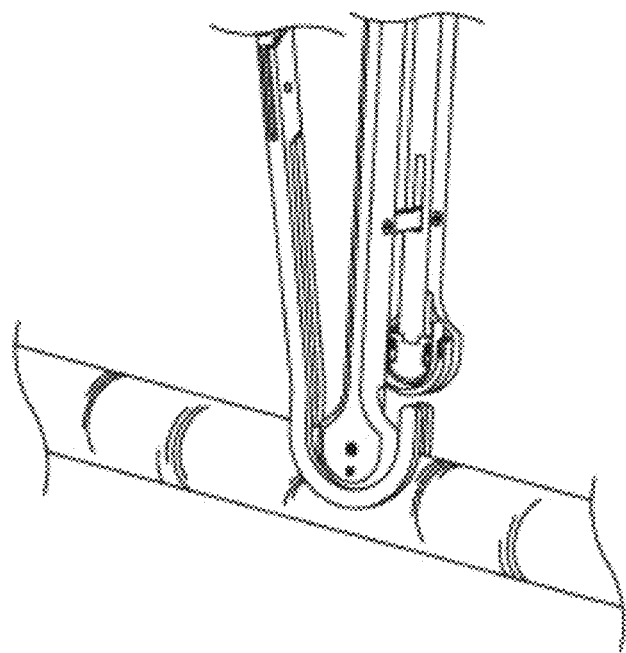
FIG. 11 is a perspective view showing a combined use of the present side-biting punch invention in conjunction with a partial clamp to achieve hemostasis during hole-making in a vascular wall.
Figure 12:
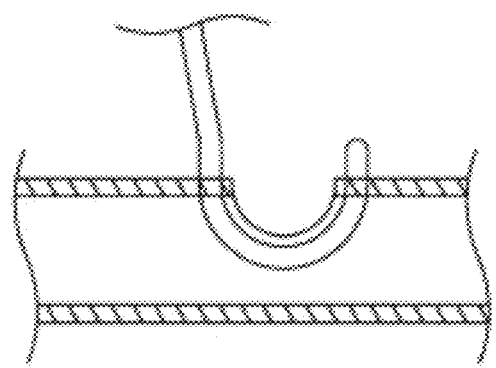
FIG. 12 shows the finite distance between the cutting line and the hemostatic zone created by partial clamping of a vessel.

Partial occlusion of a blood flow in artery or vein has been generally achieved using partial clamps. The present punch invention can conveniently work together with those clinically proven partial clamps to prevent bleeding from occurring, either during or after the hole punching. In FIG. 11 and FIG. 12 the combined use of the present invention with the partial clamp is demonstrated. First, partial clamp is applied to create a region excluded from the blood flow. Then, a side-biting vascular punch is employed to cut a piece of tissue out of this hemostatic region. The cutting line shown in FIG. 12 indicates that there is still enough margin between the hemostatic line of clamping to the periphery of the hole punched. End-to-side anastomosis can thus be safely performed by running suturing the graft end with the hole periphery, while partial clamp is locked in place to exclude the bleeding concern.

It has been generally known to vascular surgeons that the contemporary vascular punch, in the anvil-in-a-tube-cutter form, is principally based on shearing force generated via a rectilinear or a helical engagement of anvil with its receiving tube cutter Tissue separation, as a matter of fact, can only be attained for hole diameter less than 6 mm or so. For larger hole-making in a vessel, the required force increases substantially beyond the human gripping strength limit and hemostasis is generally difficult to maintain. Often, in the practical application, surgeon ought to apply numerous incremental side-biting moves on the periphery of a small hole until a desired larger hole size is achieved. As a result, the work load is high but the quality of the punched hole is not necessarily guaranteed. The present invention envisions a side-biting punch design based on a completely different normal force tissue separation principle, which can also work conveniently with partial clamp to maintain hemostasis during and after hole-making. While two embodiments are introduced and described, it is understood that those skilled in the art may devise various modifications or equivalents without departing from the spirit and scope of the invention as defined by the appended claims.

What is claimed is:

1. A vascular punch, comprising:
   a sharp razor-like cutter, having a razor-blade and a cutter seat, wherein the razor-blade is curved in a U-shape form and mounted in the cutter seat;
   a backstop element, attached with a semi-rigid pad for receiving the razor-like cutter; and
   a linkage handler, being able to engage the cutter seat and the backstop element at a distal end of the linkage handler, an engagement of a razor blade edge of the razor-blade being in alignment with a backstop surface of the backstop element;
   wherein at a proximal end of the linkage handler, a hand gripping force can be applied and transmitted through the linkage handler to a distal end of the razor-like cutter intended for cutting;
   wherein said backstop element is adjustable, which comprises the semi-rigid pad, a rigid supporting seat and a pad platform provided with a surface orientation mechanism;
   wherein said surface orientation mechanism comprises a lock screw threaded from an interior side of said backstop element, while three set screws threaded oppositely from an exterior side of the backstop element; and said three set screws can be adjusted independently to result in a full contact line formation between the razor blade edge and the semi-rigid pad.

2. The vascular punch as defined in claim 1, wherein the linkage handler is made with a four-bar linkage type handler for hand gripping and cutting force transmission; the linkage handler comprising a first elongated lever rigidly joined with the cutter seat at one end, and likewise a second elongated lever affixed with the backstop element; the first and second levers being rotatably hinged into a four-bar parallelogram linkage mechanism to bring said first lever onto said second lever forming a line contact of the razor blade edge with the backstop surface; the first and second levers being coupled to a pistol-like handle comprising a handset and a trigger, with the second lever rigidly connected to the handset whereas the first lever is slidably joined with the trigger of the pistol-like handle.

3. The vascular punch as defined in claim 2, said trigger comprising a slot at a distal end of the trigger receiving a pivot of said first lever, wherein rectilinear motion of the pivot is allowed within said slot, together with a finger arm for hand gripping and force application, and a spring element to bring said trigger at a cocked position ready for use.

4. The vascular punch as defined in claim 1, wherein the linkage handler is made with a single-pivot linkage type handler for hand gripping and cutting force transmission; the linkage handler comprising a first elongated lever rigidly joined with the cutter seat, and likewise a second elongated lever affixed with the backstop element; the first and second levers being rotatably hinged into a scissors-like linkage mechanism allowing said first lever be brought onto said second lever, forming a line contact of the razor blade edge with the backstop surface at distal ends of said first and second levers; whereas proximal ends of said first and second levers being coupled to a spring element allowing said vascular punch which is scissors-like to be opened at a ready-to-use position.

* * * * *